(12) United States Patent
Ballard et al.

(10) Patent No.: US 8,715,323 B2
(45) Date of Patent: May 6, 2014

(54) CORONAL ANGULATING CONNECTOR

(75) Inventors: Rodney R. Ballard, Lakeland, TN (US); Keith E. Miller, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 186 days.

(21) Appl. No.: 13/275,096

(22) Filed: Oct. 17, 2011

(65) Prior Publication Data

US 2013/0096617 A1  Apr. 18, 2013

(51) Int. Cl.
*A61B 17/70* (2006.01)
(52) U.S. Cl.
USPC ........................................... 606/278
(58) Field of Classification Search
USPC ......... 606/246, 250, 251, 253, 256, 260, 264, 606/265, 267, 268, 270, 272, 276, 277, 606/278; 403/362; 411/393
See application file for complete search history.

(56) References Cited

U.S. PATENT DOCUMENTS

| | | | | |
|---|---|---|---|---|
| 5,261,909 A * | 11/1993 | Sutterlin et al. | | 606/264 |
| 6,283,967 B1 | 9/2001 | Troxell et al. | | |
| 6,306,137 B2 | 10/2001 | Troxell | | |
| 2007/0270805 A1 | 11/2007 | Miller et al. | | |
| 2009/0259256 A1 | 10/2009 | Miller | | |
| 2010/0049253 A1 | 2/2010 | Miller | | |
| 2011/0106164 A1 | 5/2011 | Wilcox et al. | | |
| 2011/0172717 A1 | 7/2011 | Miller | | |
| 2011/0184462 A1 | 7/2011 | Gil et al. | | |
| 2011/0190828 A1 | 8/2011 | Null et al. | | |
| 2011/0196425 A1 | 8/2011 | Rezach et al. | | |

* cited by examiner

*Primary Examiner* — Pedro Philogene
*Assistant Examiner* — David Comstock

(57) ABSTRACT

A connector is provided for linear implants such as spinal rods which are disposed within the coronal plane of a body. The connector includes a first portion having a first cavity for disposal therethrough of a first spinal rod. A second portion has a second cavity for the disposal therethrough of a second spinal rod. The second portion is rotatable relative to the first portion. Methods of use are disclosed.

20 Claims, 3 Drawing Sheets

CORONAL ANGULATING CONNECTOR

TECHNICAL FIELD

The present disclosure generally relates to medical devices, systems and methods for the treatment of musculoskeletal disorders, and more particularly to a spinal implant fixation system that employs a connector for the linear implants to provide stabilization of vertebrae.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders include discectomy, laminectomy, fusion and implantable prosthetics. During surgical treatment, one or more rods may be attached via fasteners to the exterior of two or more vertebral members. This disclosure describes an improvement over these prior art technologies.

SUMMARY

Accordingly, an implant connector is provided that comprises a first member including a first cavity that defines a longitudinal axis along which a first implant is configured for disposal in a fixed orientation. A second member is connected to the first member along a first axis and defines a second cavity that defines a longitudinal axis along which a second implant is configured for disposal. The second cavity is rotatable about a second axis that is disposed in a transverse orientation and intersecting the longitudinal axis of the second cavity such that the second implant is rotatable in a first plane relative to the first implant.

In one embodiment, the implant connector comprises a second member rotatable within a first coronal plane about an axis of rotation which is transverse to the longitudinal second axis. In one embodiment, the implant connector comprising a first member including a first cavity that defines a longitudinal first axis along which a first rod is configured for disposal in a fixed orientation. The first cavity is generally U-shaped and has a open lateral side. A connecting portion extending from the first member and including a flat circular portion with splines at a top surface thereof. A second member extends from the connecting portion and includes a second cavity which defines a longitudinal second axis. The second member being rotatable within a first coronal plane about an axis of rotation which is transverse to the longitudinal second axis. A disk shaped collar is rotatably mounted to the connecting portion and having a splined bottom surface which abuts the top surface of the circular portion, wherein the second member is fixedly mounted to the collar.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
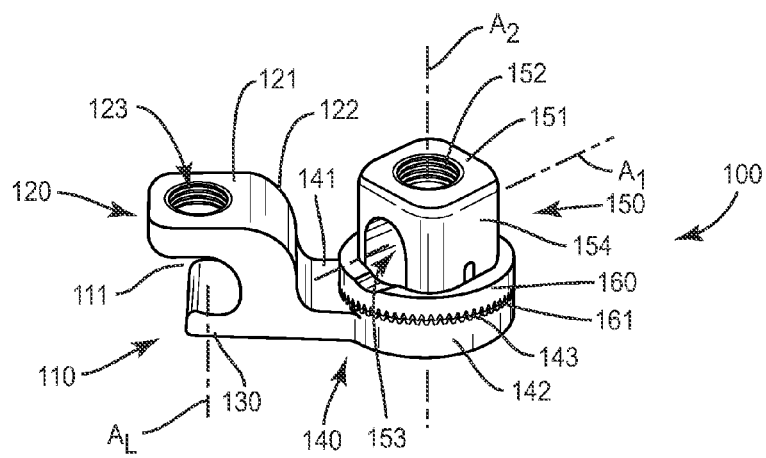
FIG. 1 is a perspective view of one embodiment of a connector in accordance with the principles of the present disclosure.

The exemplary embodiments of the connector are discussed in terms of medical devices for the treatment of musculoskeletal disorders and more particularly, in terms of an bone fastener that provides stabilization for treating a vertebral column. It is contemplated that the connector provides a robust. system and method for connecting two spinal rods. It is further contemplated that the connector allows the user to adjust and lock the coronal angulation between implants, such as, for example, vertebral rods.

In one embodiment, the connector has a side-loading connection that facilitates connection to a first, existing rod. It is envisioned that a second rod is attached to the connector with either a closed, top-loading or side loading connection. The second rod connection incorporates a splined washer that allows the second rod to be locked at different coronal angles. In one embodiment, the connector has a low profile configuration with a range of coronal adjustment. In one embodiment, the connector facilitates 360 degrees of adjustment of the second rod. It is envisioned that the term coronal plane refers to a frontal plane perpendicular to the ground, which in humans divides the body into dorsal and ventral (i.e., back and front, or posterior and anterior portions).

It is envisioned that the present disclosure maybe employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is contemplated that the disclosed connector and system may be alternatively employed in a surgical treatment with a patient in a prone or supine position, and/or employ various surgical approaches to the spine, including anterior, posterior, posterior mid-line, medial, lateral, postero-lateral, and/or antero-lateral approaches, and in other body regions. The present disclosure may also be alternatively employed with procedures for treating the lumbar, cervical, thoracic, sacral and pelvic regions of a spinal column. The connector and system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent. "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The components of the connector can be fabricated from biologically acceptable materials suitable for medical applications, including metals, synthetic polymers, ceramics and bone material and/or their composites, depending on the particular application and/or preference of a medical practitioner. For example, the components of the connector and system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers. polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the bone fastener system may have material composites, including the above materials, to achieve various desired characteristics such as strength, rigidity, elasticity. compliance, biomechanical performance, durability and radiolucency or imaging preference. The components of the bone fastener system, individually or collectively, may also be fabricated from a heterogeneous material such as a combination of two or more of the above-described materials.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and, any further application of the principles of the disclosure as described herein are contemplated as would normally occur to one skilled in the art, to which the disclosure relates. In particular, it is fully contemplated that the features, components, and/or steps described with respect to one embodiment may be combined with the features, components, and/or steps described with respect to other embodiments of the present disclosure. The following discussion includes a description of a bone fastener system and related methods of employing the bone fastener and system in accordance with the principles of the present disclosure. Alternate embodiments are also disclosed. Reference will now be made in detail to the exemplary embodiments of the present disclosure, which are illustrated in the accompanying figures.

In one embodiment, as shown in FIG. 1, the connector 100 includes a first member 110 attached to a second member 150 via a connecting portion, such as, for example, base 140. The first member 110 is configured to support and retain a first linear implant, such as, for example, a vertebral rod, within a first cavity 111 defined by an upper aim 120 and a lower arm 130. Cavity 111 is generally U-shaped and has an open lateral side. It is contemplated that the first member and/or the second member may be configured as an open receiver for disposal of a longitudinal and/or linear implant. It is further contemplated that the implant may have arcuate portions.

The lower arm 130 is positioned on the same plane as the base 140 and is substantially parallel to a top wall 121 of the upper arm, the top wall having a threaded aperture 123 configured to receive a setscrew. Upper arm 120 includes a curved portion 122, which extends between the top wall 121 and the base 140. Base 140 includes a linear portion 141 and a circular portion 142 having teeth of a splined upper surface 143 thereof. The teeth of surface 143 are circumferentially disposed about surface 143 and include a tooth and groove configuration. Second member 150 includes top wall 151 with a threaded aperture 152 configured to receive a setscrew and side walls 154. A second cavity, such as, for example, a channel 153 extends through the second member and is configured to support and retain a second linear and/or longitudinal implant, such as, for example, a vertebral rod. Channel 153 has a tubular bore configuration. Second member 150 is connected to a washer 160, which is mounted to the circular portion 142 of the base 140. Washer 160 has a toothed lower splined surface 161, which engages the splined upper surface 143 of the base. The teeth of surface 161 are circumferentially disposed about surface 161 and include a tooth and groove configuration. Surface 161 meshes with surface 143, as described below, such that the teeth of surface 143 seat with the grooves of surface 161, and the teeth of surface 161 seat with the grooves of surface 143. The washer 160 and the second member 150 are rotatable with respect to the base 140. It is envisioned that the mating splined surfaces 143 and 161 maintain the second member in a fixed position relative to the base once it has been rotated to a desired orientation.

Figure 7:
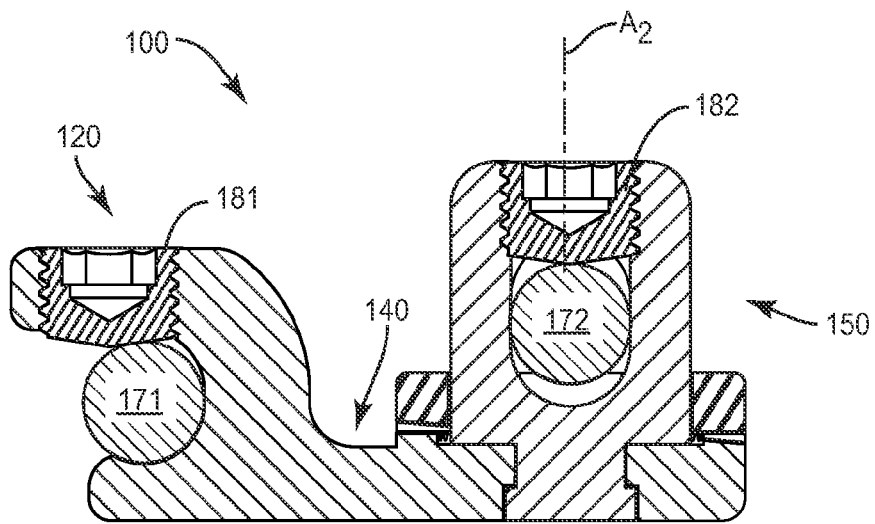
FIG. 7 is a cross section view of an implant system employing the connector shown in FIG. 1.

For example, in use, upon disposal of a second implant in a selected orientation relative to a first implant, as described below, splined surfaces 143, 161 are brought into engagement to maintain the second member in a fixed position relative to the base. As shown in FIG. 7, washer 160 protrudes into channel 153 to engage implant 172. Upon the selected orientation of the implants, a setscrew is threaded with aperture 152 and torqued onto implant 172 disposed within channel 153. The force of the setscrew against implant 172 drives the respective teeth of splined surfaces 143, 161 into fixed engagement such that second member is maintained in a fixed position relative to the base. It is envisioned that second member 150 can rotate and lock an implant at different angles in a coronal plane. It is further envisioned that the second member may be disposed with the base in alternate fixed configurations, such as, for example, friction fit, pressure fit, locking protrusion/recess, locking keyway and/or adhesive.

The cavity 111 of the first member 110 defines a longitudinal axis $A_L$ along which the first linear implant is configured for disposal in a fixed orientation. The channel 153 of the second member defines a first axis $A_1$ along which the second linear implant is disposed. It is envisioned that the second member 150 is rotatable about a second axis $A_2$, which is in a transverse orientation relative to both the longitudinal axis $A_L$ and the first axis $A_1$ such that the second implant can be rotated in the same plane, which is a coronal plane of the body in which the first implant is disposed. It is further envisioned that the second implant, disposed along first axis $A_1$, can be rotated through an angle α (FIG. 7) relative to the first implant, disposed along longitudinal axis $A_L$, in a range of approximately 75 degrees to −75 degrees, and desirably in a range of approximately 60 degrees to −60 degrees, such that implants such as vertebral rods can be angled in a first direction and a second opposing direction, such as, for example, clockwise and counter clockwise. It is further envisioned that when the implants are relatively disposed such that first axis $A_1$ is disposed at an angle α of 0 degrees from longitudinal axis $A_L$, the implants are disposed in a parallel orientation.

Figure 2:
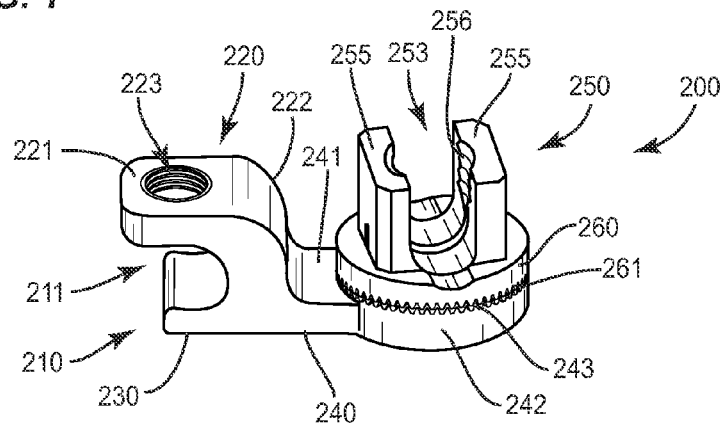
FIG. 2 is a perspective view of one embodiment of the connector shown in FIG. 1.

In one embodiment, as shown in FIG. 2, the connector 200 includes a first member 210 attached to a second member 250 via a base 240. The first member 210 is configured to support and retain a first linear implant, such as, for example, a surgical rod, within a U-shaped cavity 211 defined by an upper arm 220 and a lower arm 230. The lower arm 230 is positioned on the same plane as the base 240 and is substantially parallel to a top wall 221 of the upper arm, the top wall having a threaded aperture 223 configured to receive a setscrew. Upper arm 220 includes a curved portion 222, which extends between the top wall 221 and the base 240. Base 240 includes a linear portion 241 and a circular portion 242 having teeth on a splined upper surface 243 thereof. Second member 250 includes upright walls 255, which are parallel to each other and spaced apart so as to define a channel 253, which is configured to support and retain a second linear implant. The inner surface of each upright wall 255 has a threaded portion 256 configured to accommodate a setscrew. Second member 250 is connected to a washer 260, which is mounted to the circular portion 242 of the base 240. Washer 260 has a splined lower surface 261, which engages the splined upper surface 243 of the base 240. The washer 260 and the second member 250 are rotatable with respect to the base 240 but are maintained in a fixed relative position once rotated to a desired orientation. The respective teeth of splined surfaces 243, 261 are forced into fixed engagement such that second member 250 is maintained in a fixed position relative to base 240, similar to that described with regard to FIG. 7.

In like manner to the embodiment shown in FIG. 1, the cavity 211 of the first member 210 defines a longitudinal axis $A_L$ along which the first linear implant is configured for disposal in a fixed orientation. The channel 253 of the second member defines a first axis $A_1$ along which the second linear implant is disposed. However, the second member 250 is rotatable about a second axis $A_2$, which is in a transverse orientation relative to both the longitudinal axis $A_L$ and the first axis $A_1$ such that the second implant can be rotated in the same plane, which is a coronal plane of the body in which the first implant is disposed.

Figure 3:
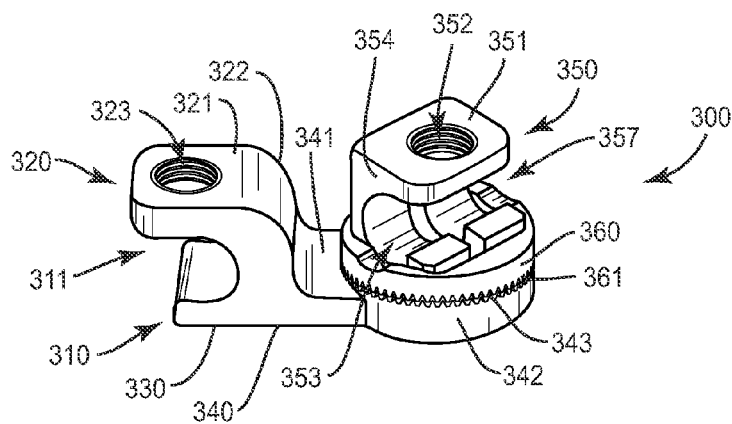
FIG. 3 is a perspective view of one embodiment. of the connector shown in FIG. 1.

In one embodiment, as shown in FIG. 3, the connector 300 includes a first member 310 attached to a second member 350 via a base 340. The first member 310 is configured to support and retain a first linear implant, i.e., a surgical rod, within a U-shaped cavity 311 defined by an upper arm 320 and a lower arm 330. The lower arm 330 is positioned on the same plane as the base 340 and is substantially parallel to a top wall 321 of the upper arm, the top wall having a threaded aperture 323 configured to receive a setscrew. Upper arm 320 includes a curved portion 322, which extends between the top wall 321 and the base 340. Base 340 includes a linear portion 341 and a circular portion 342 having teeth on a splined upper surface 343 thereof. Second member 350 includes top wall 351 with a threaded aperture 352 configured to receive a setscrew and a side wall 354. Opposite side wall 354, second member 350 includes an opening 357 to provide a side access to channel 353. Channel 353 extends through the second member and is configured to support and retain a second linear implant. Second member 350 is connected to a washer 360, which is mounted to the circular portion 342 of the base 340. Washer 360 has a splined lower surface 361, which engages the splined upper surface 343 of the base. The washer 360 and the second member 350 are rotatable with respect to the base but are maintained in a fixed relative position once rotated to a desired orientation. The respective teeth of splined surfaces 343, 361 are forced into fixed engagement such that second member 350 is maintained in a fixed position relative to base 340, similar to that described with regard to FIG. 7.

In like manner to the embodiment shown in FIG. 1, the cavity 311 of the first member 310 defines a longitudinal axis $A_L$ along which the first linear implant is configured for disposal in a fixed orientation. The channel 353 of the second member defines a first axis $A_1$ along which the second linear implant is disposed. It is contemplated that the second member 350 is rotatable about a second axis $A_2$ that is in a transverse orientation relative to both the longitudinal axis $A_L$ and the first axis $A_1$ such that the second implant can be rotated in the same plane, which is a coronal plane of the body in which the first implant is disposed.

Figure 4:
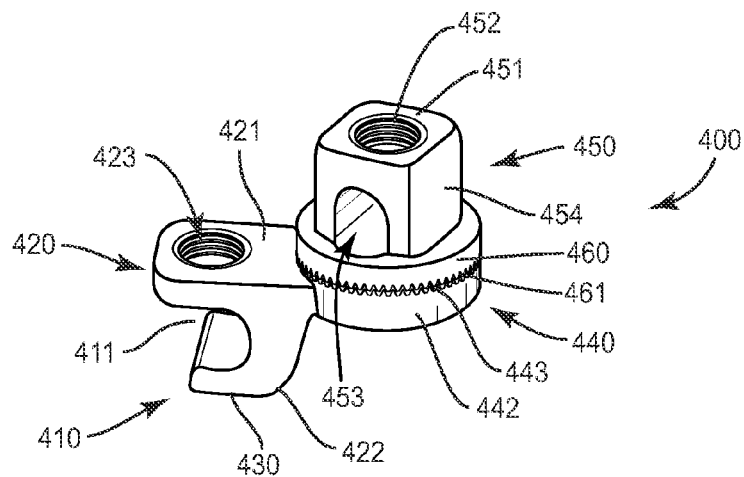
FIG. 4 is a perspective view of one embodiment of a connector in accordance with the principles of the present disclosure.

In one embodiment, as shown in FIG. 4, the connector 400 includes a first member 410 attached to a second member 450 via a base 440. The first member 410 is configured to support and retain a first linear implant, such as, for example, a surgical rod, within a U-shaped cavity 411 defined by an upper arm 420 and a lower arm 430. Unlike embodiments 100, 200 and 300, the upper arm 420 is positioned on the same plane as the base 440 and is substantially parallel to the lower arm 430, the upper arm 420 having a threaded aperture 123 configured to receive a setscrew. Lower arm 430 includes a curved portion 422, which extends to the base 440. Base 140 includes a circular portion 442 having teeth on a splined upper surface 443 thereof. Second member 450 includes top wall 451 with a threaded aperture 452 configured to receive a setscrew, and side walls 454. Channel 453 extends through the second member and is configured to support and retain a second linear implant. Second member 450 is connected to a washer 460, which is mounted to the circular portion 442 of the base 440. Washer 460 has a toothed lower surface 461, which engages the splined upper surface 443 of the base. The washer 460 and the second member 450 are rotatable with respect to the base 440 but are maintained in a fixed relative position once rotated to a desired orientation. The respective teeth of splined surfaces 443, 461 are forced into fixed engagement such that second member 450 is maintained in a fixed position relative to base 440, similar to that described with regard to FIG. 7.

The cavity 411 of the first member 410 defines a longitudinal axis $A_L$ along which the first linear implant is configured for disposal in a fixed orientation. The channel 453 of the second member defines a first axis $A_1$ along which the second linear implant is disposed. It is envisioned that the second member 450 is rotatable about a second axis $A_2$, which is in a transverse orientation relative to both the longitudinal axis $A_L$ and the first axis $A_1$ such that the second implant can be rotated in a coronal plane of the body parallel to the plane in which the first implant is disposed. It is contemplated that when the second implant is completely offset and in a plane such that the second implant does not engage the first implant, the second implant can be rotated 360 degrees without interference with the first implant. The same applies to embodiments 500 and 600 described below.

Figure 5:
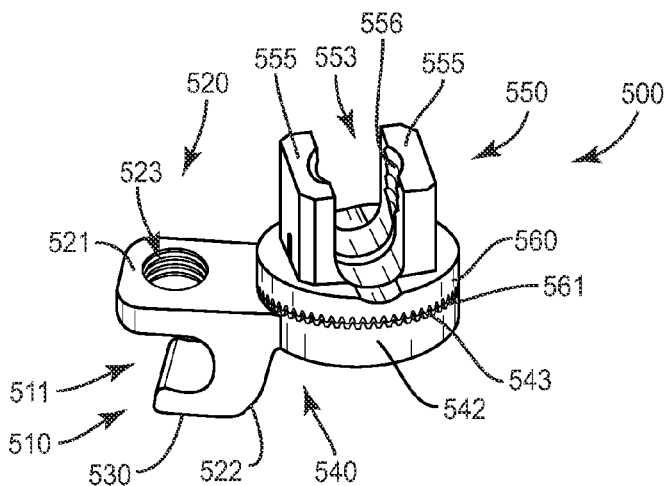
FIG. 5 is a perspective view of one embodiment of the connector shown in FIG. 4.

In one embodiment, as shown in FIG. 5, the connector 500 includes a first member 510 attached to a second member 550 via a connecting portion, such as, for example, base 540. The first member 510 is configured to support and retain a first linear implant, such as, for example, a vertebral rod, within a first cavity 511 defined by an upper arm 520 and a lower arm 530. Unlike embodiments 100, 200 and 300, upper arm 520 is positioned on the same plane as the base 540. Upper arm 520 is substantially parallel to the lower arm 530 and has a threaded aperture 523 configured to receive a setscrew. Lower arm 530 includes a curved portion 522, which extends to the base 540. Base 540 includes a circular portion 542 having teeth on a splined upper surface 543 thereof. Second member 550 includes upright walls 555 which are parallel to each other and spaced apart so as to define a channel 553 which is configured to support and retain a second linear implant. The inner surface of each upright wall 555 has a threaded portion 556 configured to accommodate a setscrew. Second member 550 is connected to a washer 560, which is mounted to the circular portion 542 of the base 540. Washer 560 has a splined lower surface 561, which engages the toothed upper surface 543 of the base 540. The washer 560 and the second member 550 are rotatable with respect to the base 540 but are maintained in a fixed relative position once rotated to a desired orientation. The respective teeth of splined surfaces 543, 561 are forced into fixed engagement such that second member 550 is maintained in a fixed position relative to base 540, similar to that. described with regard to FIG. 7.

In like manner to the embodiment shown in FIG. 4, the cavity 511 of the first member 510 defines a longitudinal axis $A_L$; along which the first linear implant is configured for disposal in a fixed orientation. The channel 553 of the second member defines a first axis $A_1$ along which the second linear implant is disposed. However, the second member 550 is rotatable about a second axis $A_2$, which is in a transverse orientation relative to both the longitudinal axis $A_L$ and the first axis $A_1$ such that the second implant can be rotated in a coronal plane of the body parallel to the plane in which the first implant is disposed.

Figure 6:
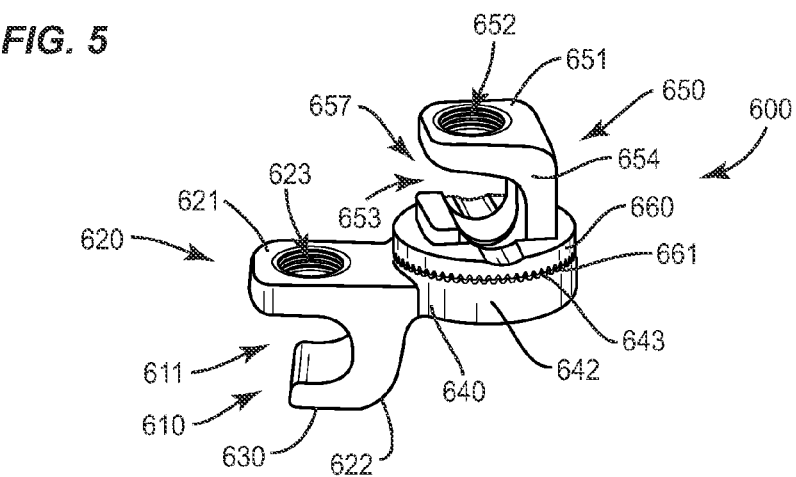
FIG. 6 is a perspective view of one embodiment of the connector shown in FIG. 4.

In one embodiment, as shown in FIG. 6, the connector 600 includes a first member 610 attached to a second member 650 via a base 640. The first member 610 is configured to support and retain a first linear implant, such as, for example, a vertebral rod, within a cavity 611 defined by an upper arm 620 and a lower arm 630. The upper arm 620 is positioned on the same plane as the base 640 and is substantially parallel to the lower arm 630, the upper arm 620 having a threaded aperture 623 configured to receive a setscrew. Lower arm 630 includes a curved portion 622, which extends to the base 640. Base 640 includes a circular portion 642 having teeth on a splined upper surface 643 thereof. Second member 650 includes top wall 651 with a threaded aperture 652 configured to receive a set screw and a side wall 654. Opposite side wall 654, second member 650 includes an opening 657 to provide a side access to channel 653. Channel 653 extends through the second member 650 and is configured to support and retain a second linear implant. Second member 650 is connected to a washer 660, which is mounted to the circular portion 642 of the base 640. Washer 660 has a splined lower surface 661, which engages the splined upper surface 643 of the base. The washer 660 and the second member 650 are rotatable with respect to the base 640. The respective teeth of splined surfaces 643, 661 are forced into fixed engagement such that second member 650 is maintained in a fixed position relative to base 640, similar to that described with regard to FIG. 7.

In like manner to the embodiment shown in FIG. 4, the cavity 611 of the first member 610 defines a longitudinal axis $A_L$ along which the first linear implant is configured for disposal in a fixed orientation. The channel 653 of the second member defines a first axis $A_1$ along which the second linear implant is disposed. It is contemplated that the second member 650 is rotatable about a second axis $A_2$, which is in a transverse orientation relative to both the longitudinal axis $A_L$ and the first axis $A_1$ such that the second implant can be rotated in a coronal plane of the body parallel to the plane in which the first implant is disposed.

Figure 8:
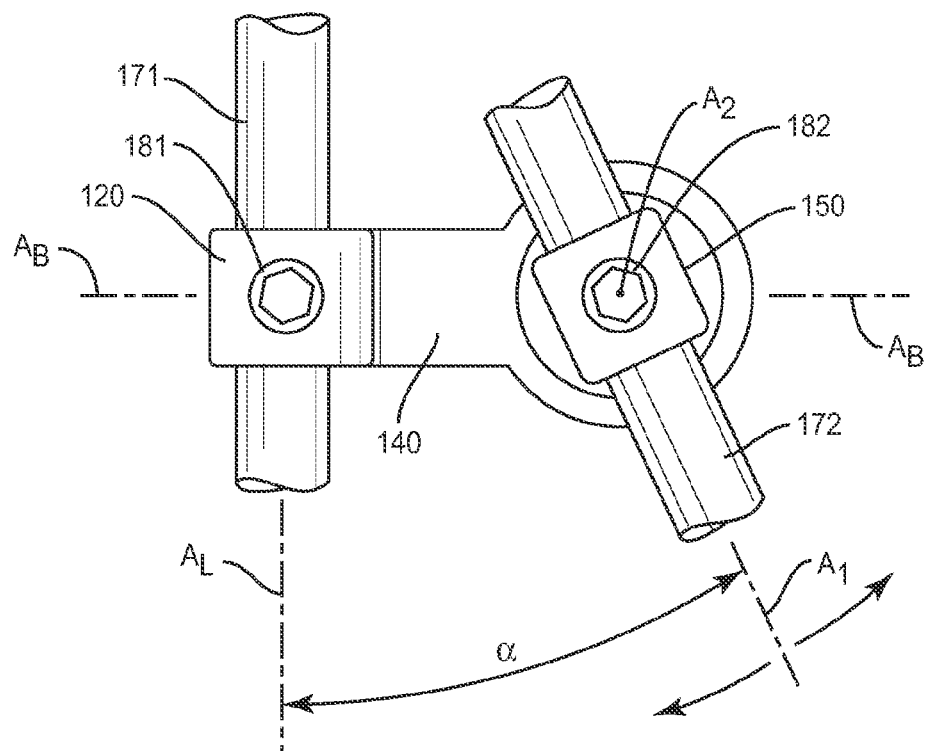
FIG. 8 is a plan view of the implant system employing the connector of FIG. 1.

Referring now to FIGS. 7 and 8. the connector 100 is shown in a system, which includes linear implants 171 and 172, and set screws 181 and 182. The second implant can be rotated with respect to the first implant within a coronal plane, for example, the plane of the paper as seen in FIG. 8, in a first direction and a second opposing direction, such as, for example, clockwise and counter clockwise. In one embodiment, the planes of rotation of the linear implants can be the same, or as described above with respect to embodiments 400, 500 and 600, they can be spaced apart, staggered and/or offset from, but oriented parallel to each other, both of them being oriented in a coronal plane of the body. As mentioned above, the second implant is rotated in a plane in which the first implant is disposed (embodiments 100, 200 and 300). The second implant, disposed along first axis $A_1$, can be rotated through an angle α relative to the first implant, disposed along longitudinal axis $A_L$, in a range of approximately 75 degrees to −75 degrees and avoid interference with the first implant. It is contemplated that such interference is caused by engagement of the second implant with the first implant as the second implant rotates, which limits rotation of the implant beyond the range of rotation in a plane, such as, for example, a coronal plane. It is further contemplated that the implants may be offset, minimally or slightly, such that the first implant is disposed in a first plane and the second implant is disposed in a second plane, and interference is caused by engagement of the second implant with the first implant as the second implant rotates. It is further contemplated that to avoid interference and engagement of the second implant with the first implant as the second implant rotates, the second implant is disposed in a plane and the first implant is disposed in a plane, such that the planes are sufficiently offset to allow free and/or non-interfering rotation of the second implant relative to the first implant. For example, if the plane in rotation of the second implant is sufficiently spaced apart, staggered and/or offset from the plane in which first implant is disposed (embodiments 400, 500 and 600) the second implant can be rotated an angle α of 360 degrees relative to the first implant, such that the profile of the connector is higher.

As can be seen in FIG. 8, the base 140 defines an axis $A_B$ which is transverse to the longitudinal axis $A_L$ along which the first implant is disposed. Axis $A_2$ around which the second member 150 is rotated is transverse to and intersects both the axis $A_1$ along which the second implant is disposed and the axis $A_B$ of the base.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An implant connector comprising:
    a first member including a first cavity that defines a longitudinal axis along which a first implant is configured for disposal in a fixed orientation; and
    a second member connected to the first member along a first axis and defining a second cavity, the second cavity comprising a U-shaped configuration with an open top portion that faces away from the first member and defines a longitudinal axis along which a second implant is configured for disposal, the second cavity being rotatable about a second axis that is disposed in a transverse orientation and intersecting the longitudinal axis of the second cavity such that the second implant is rotatable in a first plane relative to the first implant.

2. An implant connector according to claim 1, wherein the first member further includes a lateral opening in communication with the first cavity and disposed for receiving the first implant.

3. An implant connector according to claim 1, wherein the second member includes a splined configuration for securing the second cavity in a selected angular configuration with respect to the first member.

4. An implant connector according to claim 1, wherein the open top portion of the second member includes a threaded configuration.

5. An implant connector according to claim 1, wherein the second member includes a lateral opening.

6. An implant connector according to claim 1, wherein the longitudinal axis of the first cavity and the longitudinal axis of the second cavity are both disposed in a first plane.

7. An implant connector according to claim 1, wherein the transverse second axis intersects the first axis.

8. An implant connector according to claim 1, wherein the longitudinal axis of second cavity is rotatable through an angle from about 75 to about −75 degrees.

9. An implant connector according to claim 1, wherein the first implant is disposed in a second plane spaced apart and parallel to the first plane.

10. An implant connector according to claim 1, wherein the first plane is a coronal plane of a body.

11. An implant connector according to claim 1, wherein the first member comprises a distal side facing a vertebral body and a proximal side facing away from a vertebral body and the second member is disposed with the proximal side.

12. An implant connector comprising:
    a first member including a first cavity that defines a longitudinal first axis along which a first rod is configured for disposal in a fixed orientation; and
    a connecting portion extending from the first member; and
    a second member extending from the connecting portion and including a second cavity which defines a longitudinal second axis, the second member being rotatable within a first coronal plane about an axis of rotation which is transverse to the longitudinal second axis, wherein the second cavity has a U-shaped configuration with an open top portion that faces away from the first member.

13. An implant connector according to claim 12, wherein the longitudinal first axis is disposed within the first coronal plane.

14. An implant connector according to claim 13, wherein the longitudinal second axis of the second cavity is rotatable through an angle from about 60 to about −60 degrees.

15. An implant connector according to claim 12, wherein the longitudinal first axis is disposed within a second coronal plane which is spaced apart from but parallel to the first coronal plane.

16. An implant connector according to claim 15, wherein the longitudinal second axis is rotatable from 0 to 360 degrees.

17. An implant connector according to claim 12, wherein the second member includes a splined configuration for securing the second cavity in a selected angular configuration with respect to the first member.

18. An implant connector according to claim 12, wherein the configuration of the second member comprises two spaced apart upright arms, the upright arms having a threaded inner surface.

19. An implant connector according to claim 12, wherein the connecting portion comprises a distal side facing a vertebral body and a proximal side facing away from a vertebral body and the second member is disposed with the proximal side.

20. An implant connector comprising:
    a first member including a first cavity that defines a longitudinal first axis along which a first rod is configured for disposal in a fixed orientation, the first cavity comprising a first U-shaped configuration having an open lateral side;
    a connecting portion extending from the first member and including a flat circular portion with splines at a top surface thereof;
    a second member extending from the connecting portion and including a second cavity, the second cavity comprising a second U-shaped configuration with an open top portion that faces away from the first member and defines a longitudinal second axis, the second member being rotatable within a first coronal plane about an axis of rotation which is transverse to the longitudinal second axis; and a disk shaped collar rotatably mounted to the connecting portion and having a splined bottom surface which abuts the top surface of the circular portion, wherein the second member is fixedly mounted to the collar.

* * * * *